US00PP21979P3

(12) United States Plant Patent
Danziger

(10) Patent No.: US PP21,979 P3
(45) Date of Patent: Jun. 14, 2011

(54) ***ANGELONIA* PLANT NAMED 'DANALON5'**

(50) Latin Name: *Angelonia angustifolia*
Varietal Denomination: DANALON5

(75) Inventor: Gabriel Danziger, Beit Dagan (IL)

(73) Assignee: Danziger "Dan FlowerFarm" (IL)

( * ) Notice: Subject to any disclaimer, the term of this patent is extended or adjusted under 35 U.S.C. 154(b) by 0 days.

(21) Appl. No.: 12/454,555

(22) Filed: May 18, 2009

(65) Prior Publication Data

US 2010/0293689 P1 Nov. 18, 2010

(51) Int. Cl.
*A01H 5/00* (2006.01)

(52) U.S. Cl. ..... Plt./404

(58) Field of Classification Search ..... Plt./404
See application file for complete search history.

*Primary Examiner* — June Hwu

(57) ABSTRACT

A new and distinct *Angelonia* cultivar named 'DANALON5' is disclosed, characterized by having a compact plant habit, exceptionally free branching and small lavender flowers. The new variety is an *Angelonia,* normally produced as an outdoor garden or container plant.

2 Drawing Sheets

Figure 1:
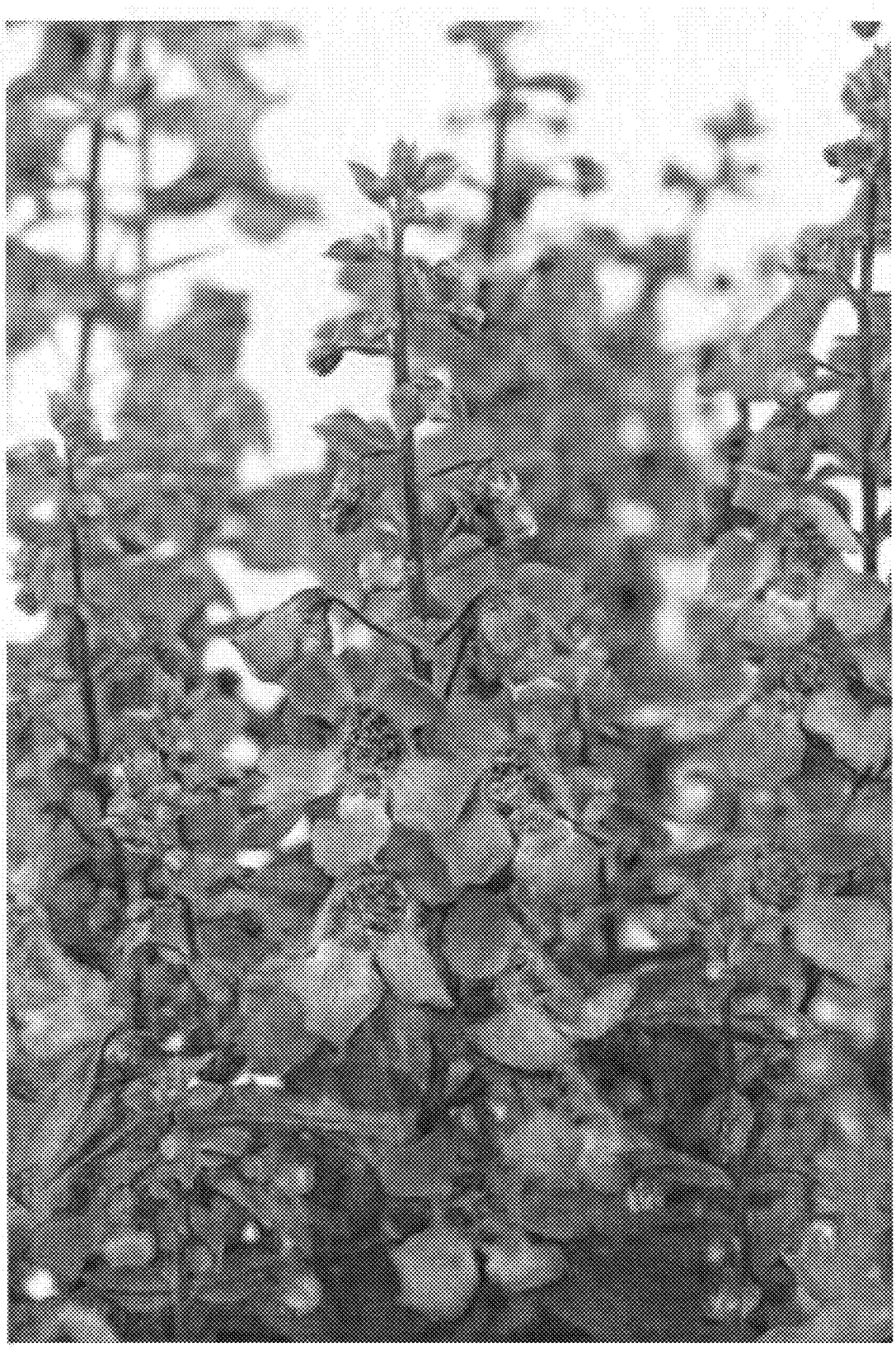

Latin name of the genus and species: *Angelonia angustifolia.*

Variety denomination: 'DANALON5'.

BACKGROUND OF THE INVENTION

The new *Angelonia* cultivar is a product of a planned breeding program conducted by the inventor, Gabriel Danziger, in Moshav Mishmar Hashiva, Israel. The objective of the breeding program was to produce new varieties of *Angelonia* for commercial introduction. The crossing resulting in the new cultivar was made in January 2007. The seed parent is the unpatented, proprietary variety referred to as *Angelonia angustifolia* 'AL-393.' The pollen parent is the unpatented, proprietary variety referred to as *Angelonia angustifolia* 'AL-42.' The new variety was discovered in May 2007 by the inventor in a group of seedlings resulting from that crossing, in a commercial greenhouse in Moshav Mishmar Hashiva, Israel.

Asexual reproduction of the new cultivar 'DANALON5' by vegetative cuttings was first performed at a commercial greenhouse in Moshav Mishmar Hashiva, Israel in May 2007. Subsequent propagation has shown that the unique features of this cultivar are stable and reproduced true to type on successive generations.

SUMMARY OF THE INVENTION

The cultivar 'DANALON5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANALON5.' These characteristics in combination distinguish 'DANALON5' as a new and distinct *Angelonia* cultivar:

1. Compact, mounded plant habit.
2. Small lavender flowers.
3. Exceptionally free branching.

PARENTAL COMPARISON

Plants of the new cultivar 'DANALON5' are similar to plants of the seed parent, 'AL-393' in most horticultural characteristics, however, plants of the new cultivar 'DANALON5' have a more compact plant habit, more freely branching and have a different color flower.

Plants of the new cultivar 'DANALON5' are similar to plants of the pollen parent, 'AL-42' in most horticultural characteristics, however, plants of the new cultivar 'DANALON5' have a different plant habit, more freely branching and have a different color flower. Additionally, flowers produced by the new variety are smaller than those of the pollen parent.

COMMERCIAL COMPARISON

Plants of the new cultivar 'DANALON5' can be compared to the commercial variety 'DANGELONI3,' U.S. Plant Pat. No. 19,456. Plants of 'DANALON5' are similar to plants of 'DANGELONI3', in most horticultural characteristics, however, plants of the new cultivar 'DANALON5' have a different color flower.

Plants of the new cultivar 'DANALON5' can be compared to the commercial variety 'DANGELONI4,' U.S. Plant Pat. No. 19,451. Plants of 'DANALON5' are similar to plants of 'DANGELONI4', in most horticultural characteristics, however, plants of the new cultivar 'DANALON5' have more free branching habit and a different color flower.

BRIEF DESCRIPTION OF THE PHOTOGRAPH

The accompanying photographs in FIG. 1 illustrates in full color a typical close view flower of 'DANALON5.'

Figure 2:
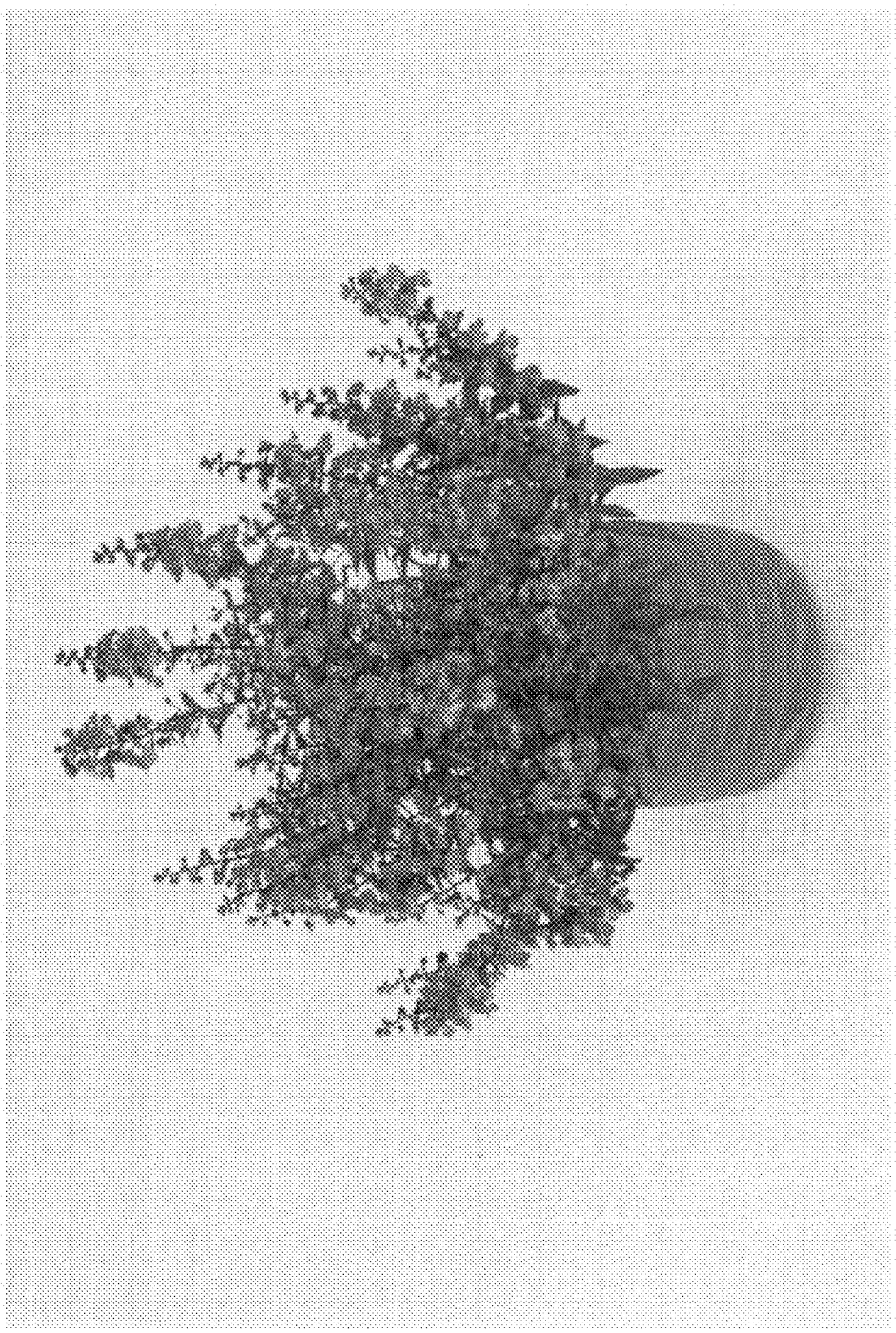

FIG. 2 illustrates in full color a typical plant of 'DANALON5' grown in a greenhouse, in a 13 cm pot. Age of the plant photographed is approximately 8 weeks from a rooted cutting, with 1 rooted cutting planted in the pot shown.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANALON5' plants grown in a greenhouse in Moshav Mishmar Hashiva, Israel. The growing temperature ranged from day temperatures of 22° C. to 32° C., and night temperatures of 18° C. to 23° C. The greenhouse is un-shaded, giving bright, normal sunlight conditions. No growth regulators or artificial light treatments were given. Measurements and numerical values represent averages of typical plant types.

Botanical classification. *Angelonia angustifolia* cultivar 'DANALON5.'

PROPAGATION

Time to Initiate Roots: About 10 to 14 days at approximately 25° C.

Root Description: Fibrous.

PLANT

Growth Habit: Mounded

Pot size of plant described: 13 cm.

Height:

*To top of foliage.*—Approximately 20 cm.

*To top of flowers.*—Approximately 25 cm.

Plant Spread: Approximately 25 cm.

Growth Rate: Moderate.

Branching Characteristics: Very free branching.

Length of Primary Lateral Branches: Averages between 15-20 cm.

Diameter of Lateral Branches: Averages between 0.2-0.4 cm.

Quantity of Primary Lateral Branches: 30-40.

Characteristics of Primary Lateral Branches:

*Diameter.*—Approximately 0.2 cm.

*Color.*—Near RHS Green 139A.

*Texture.*—Glabrous.

*Strength.*—Strong, flexible.

Internodes length: 1.5-3.5 cm.

FOLIAGE

Leaf:

*Arrangement.*—Opposite.

*Quantity.*—Approximately 16 per branch.

*Average Length.*—Averages between 2-4 cm.

*Average Width.*—Averages between 0.8-1.4 cm.

*Shape of blade.*—Oblanceolate

*Apex.*—Obtuse.

*Base.*—Acute.

*Margin.*—Scalloped.

*Texture of top surface.*—Glabrous.

*Pubescence.*—Glabrous.

*Aspect.*—Flat.

*Color.*—Young foliage upper side: RHS Green 138B Young foliage under side: RHS Green 138C Mature foliage upper side: RHS Green 139A Mature foliage under side: RHS Green 138A.

*Venation.*—Type: Pinnate Venation color upper side: RHS Green 138A Venation color under side: RHS Green 138B.

*Petiole.*—No Petiole

FLOWER

Natural flowering season: April-November.

Days to flowering from rooted cutting: Approximately 14-20 days

Inflorescence and flower type and habit: Raceme inflorescence and single bilabiate flower

*Length of Inflorescence.*—11 cm Average.

*Width of Inflorescence.*—5.2 cm Average.

*Quantity of Flowers per Inflorescence.*—An average of at 15 fully open flowers at any time, and approximate 10 unopened buds.

Rate of flower opening: 3 to 6 days from bud to fully opened flower.

Flower Longevity on Plant: Individual flowers last an average of 6 days.

Persistent or Self-Cleaning: Persistent

Bud:

*Shape.*—Oblate.

*Length.*—0.6 cm.

*Diameter.*—0.6 cm.

*Color.*—Near RHS Violet 84A.

Flower size:

*Diameter.*—Approximately 1.8 cm.

*Length.*—Approximately 2.2 cm.

*Flower Tube Length.*—Approximately 1.9.

Petals.

*Length.*—0.6 cm.

*Diameter.*—0.6 cm.

*Quantity.*—5.

*Texture.*—Glabrous.

*Apex.*—Blunt.

Color:

*When opening.*—Upper surface: Near RHS Violet-Blue 94C with speckles in throat near Purple 79A. Lower surface: Near RHS Violet-Blue 94C.

*Fully opened.*—Upper surface: Near RHS Violet-Blue 94C with speckles in throat near Purple 79B. Lower surface: Near RHS Violet-Blue 94C Palate color: Near RHS Violet-Blue 94D Outer flower tube color: Near RHS Violet-Blue 92D.

Sepals:

*Quantity per flower.*—5.

*Shape.*—Acute.

*Length.*—0.2 cm.

*Width.*—Averages between 0.01-0.05 cm.

*Apex.*—Acute.

*Base.*—Truncate.

*Margin.*—Entire.

*Texture.*—Glabrous.

*Color.*—Near RHS Violet-Blue N92B.

Pedicel:

*Length.*—1.3 cm.

*Diameter.*—0.1 cm.

*Color.*—Near RHS Purple N79B.

*Strength.*—Flexible.

*Angle.*—45° C.

Peduncle:

*Length.*—Approximatelty 6.2 cm.

*Diameter.*—Approximately 0.5 cm.

*Color.*—Near RHS Purple N78BC.

*Strength.*—Flexible.

*Angle.*—90° C.

Fragrance: No

REPRODUCTIVE ORGANS

Stamens:

*Number.*—4.

*Filament length.*—2 mm.

Anthers:

*Shape.*—Oblong.

*Length.*—1.5 mm.

*Color.*—Near RHS Yellow 11D.

Pollen:

*Color.*—Near RHS Yellow 11D.

*Quantity.*—Scant.

Pistil:

*Number.*—1.

*Length.*—0.2 cm.

*Styles.*—Length: 0.15 cm Color: Near RHS Purple 75D.

*Stigma.*—Shape: Conical Color: Near RHS Purple 75D.

OTHER CHARACTERISTICS

Seeds and fruits: 10 to 20 round seeds, near RHS Brown 200B color, when mature.

Disease/pest resistance: Neither resistance nor susceptibility to normal pests and disease of *Angelonia* have been observed.

Temperature tolerance: The new variety tolerates temperatures between 8 to 35° C.

What is claimed is:

1. A new and distinct cultivar of *Angelonia* plant named 'DANALON5' as herein illustrated and described.

* * * * *